(12) United States Patent
Surti

(10) Patent No.: US 8,740,937 B2
(45) Date of Patent: Jun. 3, 2014

(54) SUTURE LOCK

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1193 days.

(21) Appl. No.: 12/125,525

(22) Filed: May 22, 2008

(65) Prior Publication Data

US 2008/0300629 A1  Dec. 4, 2008

Related U.S. Application Data

(60) Provisional application No. 60/941,086, filed on May 31, 2007.

(51) Int. Cl.
*A61B 17/04* (2006.01)

(52) U.S. Cl.
USPC ........................................................ 606/232

(58) Field of Classification Search
USPC .............................. 606/72, 73, 232; 623/13.14
See application file for complete search history.

(56) References Cited

U.S. PATENT DOCUMENTS

| | | | |
|---|---|---|---|
| 1,521,396 A | 12/1924 | Scott | |
| 2,199,025 A | 4/1940 | Conn | |
| 2,609,155 A | 9/1952 | Fosnaugh | |
| 2,880,728 A | 4/1959 | Rights | |
| 3,470,875 A | 10/1969 | Johnson | |
| 3,513,848 A | 5/1970 | Winston et al. | |
| 3,556,079 A | 1/1971 | Omizo | |
| 3,664,345 A | 5/1972 | Dabbs et al. | |
| 3,710,400 A | 1/1973 | Sparks | |
| 3,856,016 A | 12/1974 | Davis | |
| 3,870,048 A | 3/1975 | Yoon | |
| 3,911,923 A | 10/1975 | Yoon | |
| 3,954,108 A | 5/1976 | Davis | |
| 3,967,625 A | 7/1976 | Yoon | |
| 3,989,049 A | 11/1976 | Yoon | |
| 4,085,743 A | 4/1978 | Yoon | |
| 4,103,680 A | 8/1978 | Yoon | |
| 4,235,238 A | 11/1980 | Ogiu et al. | |
| 4,236,470 A | 12/1980 | Stenson | |
| 4,374,523 A | 2/1983 | Yoon | |
| 4,448,194 A | 5/1984 | DiGiovanni et al. | |
| 4,539,716 A | 9/1985 | Bell | |
| 4,635,638 A | 1/1987 | Weintraub et al. | |
| 4,738,740 A | 4/1988 | Pinchuk et al. | |

(Continued)

OTHER PUBLICATIONS

International Search Report and Written Opinion dated (Aug. 13, 2008) PCT/US98/064513.

*Primary Examiner* — Melanie Tyson
(74) *Attorney, Agent, or Firm* — Brinks Gilson & Lione

(57) ABSTRACT

Suture locks, as well as related systems and methods, are provided for fixing strands of one or more sutures relative to tissue. The suture locks, systems and methods are simple and reliable in use, facilitate complete perforation closure and adjustment of the suture strands, and are adaptable to a variety of suture fixation and perforation closure situations. The suture lock includes a locking pin and a retaining sleeve. The locking pin has a main body and a grip. The retaining sleeve has a tubular body with an internal wall defining an internal passageway sized to receive the locking pin therein. The suture lock is operable between a locked configuration and unlocked configuration. In the locked configuration, the suture strands are compressed between the grip and the internal wall of the tubular body.

19 Claims, 5 Drawing Sheets

(56) References Cited

U.S. PATENT DOCUMENTS

| | | |
|---|---|---|
| 4,749,114 A | 6/1988 | Green |
| 4,773,420 A | 9/1988 | Green |
| 4,798,606 A | 1/1989 | Pinchuk |
| 4,821,939 A | 4/1989 | Green |
| 4,890,615 A | 1/1990 | Caspari et al. |
| 4,927,410 A | 5/1990 | Kovacs |
| 5,015,250 A | 5/1991 | Foster |
| 5,053,043 A | 10/1991 | Gottesman et al. |
| 5,059,201 A | 10/1991 | Asnis |
| 5,084,057 A | 1/1992 | Green et al. |
| 5,123,914 A | 6/1992 | Cope |
| 5,203,787 A | 4/1993 | Noblitt et al. |
| 5,222,508 A | 6/1993 | Contarini |
| 5,254,126 A | 10/1993 | Filipi et al. |
| 5,258,000 A | 11/1993 | Gianturco |
| 5,281,237 A | 1/1994 | Gimpelson |
| 5,304,184 A | 4/1994 | Hathaway et al. |
| 5,310,407 A | 5/1994 | Casale |
| 5,316,543 A | 5/1994 | Eberbach |
| 5,318,221 A | 6/1994 | Green et al. |
| 5,320,630 A | 6/1994 | Ahmed |
| 5,320,632 A | 6/1994 | Heidmueller |
| 5,336,229 A | 8/1994 | Noda |
| 5,350,385 A | 9/1994 | Christy |
| 5,364,408 A | 11/1994 | Gordon |
| 5,366,460 A | 11/1994 | Eberbach |
| 5,366,480 A | 11/1994 | Corriveau et al. |
| 5,368,599 A | 11/1994 | Hirsch et al. |
| 5,368,601 A | 11/1994 | Sauer et al. |
| 5,374,275 A | 12/1994 | Bradley et al. |
| 5,376,096 A | 12/1994 | Foster |
| 5,389,103 A | 2/1995 | Melzer et al. |
| 5,391,182 A | 2/1995 | Chin |
| 5,395,381 A | 3/1995 | Green et al. |
| 5,397,331 A | 3/1995 | Himpens et al. |
| 5,403,329 A | 4/1995 | Hinchcliffe |
| 5,403,342 A | 4/1995 | Tovey et al. |
| 5,405,072 A | 4/1995 | Zlock et al. |
| 5,405,354 A | 4/1995 | Sarrett |
| 5,417,691 A | 5/1995 | Hayhurst |
| 5,417,699 A | 5/1995 | Klein et al. |
| 5,423,860 A | 6/1995 | Lizardi et al. |
| 5,439,469 A | 8/1995 | Heaven et al. |
| 5,462,558 A | 10/1995 | Kolesa et al. |
| 5,462,561 A | 10/1995 | Voda |
| 5,464,427 A | 11/1995 | Curtis et al. |
| 5,470,338 A | 11/1995 | Whitfield et al. |
| 5,476,469 A | 12/1995 | Hathaway et al. |
| 5,478,353 A | 12/1995 | Yoon |
| 5,484,451 A | 1/1996 | Akopov et al. |
| 5,486,197 A | 1/1996 | Le et al. |
| 5,503,623 A | 4/1996 | Tilton, Jr. |
| 5,507,754 A | 4/1996 | Green et al. |
| 5,520,700 A | 5/1996 | Beyar et al. |
| 5,527,343 A | 6/1996 | Bonutti |
| 5,531,763 A | 7/1996 | Mastri et al. |
| 5,549,617 A | 8/1996 | Green et al. |
| 5,554,183 A | 9/1996 | Nazari |
| 5,556,402 A | 9/1996 | Xu |
| 5,562,683 A | 10/1996 | Chan |
| 5,562,688 A | 10/1996 | Riza |
| 5,571,090 A | 11/1996 | Sherts |
| 5,571,119 A | 11/1996 | Atala |
| 5,573,540 A | 11/1996 | Yoon |
| 5,573,543 A | 11/1996 | Akopov et al. |
| 5,578,044 A | 11/1996 | Gordon et al. |
| 5,584,835 A | 12/1996 | Greenfield |
| 5,586,986 A | 12/1996 | Hinchliffe |
| 5,609,597 A | 3/1997 | Lehrer |
| 5,626,590 A | 5/1997 | Wilk |
| 5,630,824 A | 5/1997 | Hart |
| 5,643,292 A | 7/1997 | Hart |
| 5,643,317 A | 7/1997 | Pavcnik et al. |
| 5,645,552 A | 7/1997 | Sherts |
| 5,653,717 A | 8/1997 | Ko et al. |
| 5,683,402 A | 11/1997 | Cosgrove et al. |
| 5,690,656 A | 11/1997 | Cope et al. |
| 5,693,060 A | 12/1997 | Martin |
| 5,700,273 A | 12/1997 | Buelna et al. |
| 5,707,379 A | 1/1998 | Fleenor et al. |
| 5,709,694 A | 1/1998 | Greenberg et al. |
| 5,728,113 A | 3/1998 | Sherts |
| 5,741,277 A | 4/1998 | Gordon et al. |
| 5,741,278 A | 4/1998 | Stevens |
| 5,746,751 A | 5/1998 | Sherts |
| 5,769,862 A | 6/1998 | Kammerer et al. |
| 5,788,625 A | 8/1998 | Plouhar et al. |
| 5,792,153 A | 8/1998 | Swain et al. |
| 5,810,848 A | 9/1998 | Hayhurst |
| 5,824,010 A | 10/1998 | McDonald |
| 5,836,955 A | 11/1998 | Buelna et al. |
| 5,836,956 A | 11/1998 | Buelna et al. |
| 5,846,253 A | 12/1998 | Buelna et al. |
| 5,860,990 A | 1/1999 | Nobis et al. |
| 5,865,791 A | 2/1999 | Whayne et al. |
| 5,865,836 A | 2/1999 | Miller |
| 5,891,159 A | 4/1999 | Sherman et al. |
| 5,902,228 A | 5/1999 | Schulsinger et al. |
| 5,908,428 A | 6/1999 | Scirica et al. |
| 5,919,184 A | 7/1999 | Tilton, Jr. |
| 5,931,844 A | 8/1999 | Thompson et al. |
| 5,938,668 A | 8/1999 | Scirica et al. |
| 5,947,997 A | 9/1999 | Pavcnik et al. |
| 5,948,000 A | 9/1999 | Larsen et al. |
| 5,957,937 A | 9/1999 | Yoon |
| 6,010,525 A | 1/2000 | Bonutti et al. |
| 6,036,699 A | 3/2000 | Andreas et al. |
| 6,068,648 A | 5/2000 | Cole et al. |
| 6,077,217 A | 6/2000 | Love et al. |
| 6,086,601 A | 7/2000 | Yoon |
| 6,086,608 A * | 7/2000 | Ek et al. ................... 606/232 |
| 6,099,553 A | 8/2000 | Hart et al. |
| 6,110,183 A | 8/2000 | Cope |
| RE36,974 E | 11/2000 | Bonutti |
| 6,200,329 B1 | 3/2001 | Fung et al. |
| 6,290,674 B1 | 9/2001 | Roue et al. |
| 6,328,727 B1 | 12/2001 | Frazier et al. |
| 6,348,059 B1 | 2/2002 | Hathaway et al. |
| 6,355,050 B1 | 3/2002 | Andreas et al. |
| 6,419,669 B1 | 7/2002 | Frazier et al. |
| 6,423,087 B1 | 7/2002 | Sawada |
| 6,491,707 B2 | 12/2002 | Makower et al. |
| 6,572,629 B2 | 6/2003 | Kalloo et al. |
| 6,592,559 B1 | 7/2003 | Pakter et al. |
| 6,610,026 B2 | 8/2003 | Cragg et al. |
| 6,641,557 B1 | 11/2003 | Frazier et al. |
| 6,699,263 B2 | 3/2004 | Cope |
| 6,712,804 B2 | 3/2004 | Roue et al. |
| 6,719,763 B2 | 4/2004 | Chung et al. |
| 6,746,472 B2 | 6/2004 | Frazier et al. |
| 6,755,843 B2 | 6/2004 | Chung et al. |
| 775,985 A1 | 11/2004 | McKain |
| 6,840,953 B2 * | 1/2005 | Martinek ................... 606/232 |
| 6,955,643 B2 | 10/2005 | Gellman et al. |
| 6,972,027 B2 | 12/2005 | Fallin et al. |
| 6,974,466 B2 | 12/2005 | Ahmed et al. |
| 6,988,987 B2 | 1/2006 | Ishikawa |
| 6,997,931 B2 | 2/2006 | Sauer et al. |
| 7,025,756 B2 | 4/2006 | Frazier et al. |
| 7,033,379 B2 | 4/2006 | Peterson |
| 7,033,380 B2 | 4/2006 | Schwartz et al. |
| 7,056,325 B1 | 6/2006 | Makower et al. |
| 7,060,078 B2 | 6/2006 | Hathaway et al. |
| 7,060,084 B1 | 6/2006 | Loshakove et al. |
| 7,074,203 B1 * | 7/2006 | Johanson et al. .............. 602/72 |
| 7,081,124 B2 | 7/2006 | Sancoff et al. |
| 7,087,073 B2 | 8/2006 | Bonutti |
| 7,101,862 B2 | 9/2006 | Cochrum et al. |
| 7,112,207 B2 | 9/2006 | Allen et al. |
| 7,115,110 B2 | 10/2006 | Frazier et al. |
| 7,118,583 B2 | 10/2006 | O'Quinn et al. |
| 7,122,039 B2 | 10/2006 | Chu |
| 7,122,040 B2 | 10/2006 | Hill et al. |
| 7,144,401 B2 | 12/2006 | Yamamoto et al. |

(56) References Cited

U.S. PATENT DOCUMENTS

| | | | |
|---|---|---|---|
| 7,156,880 B2 | 1/2007 | Evans et al. | |
| 7,157,636 B2 | 1/2007 | Hsieh | |
| 7,166,116 B2 | 1/2007 | Lizardi et al. | |
| 7,175,636 B2 | 2/2007 | Yamamoto et al. | |
| 7,217,279 B2 | 5/2007 | Reese | |
| 7,232,448 B2 | 6/2007 | Battles et al. | |
| RE39,841 E | 9/2007 | Bilotti | |
| 7,273,451 B2 | 9/2007 | Sekine et al. | |
| 7,300,451 B2 | 11/2007 | Crombie et al. | |
| 7,316,706 B2 * | 1/2008 | Bloom et al. | 606/232 |
| 7,323,004 B2 | 1/2008 | Parahar | |
| 7,326,221 B2 | 2/2008 | Sakamoto | |
| 7,331,968 B2 | 2/2008 | Arp et al. | |
| 7,335,221 B2 | 2/2008 | Collier et al. | |
| 7,344,545 B2 | 3/2008 | Takemoto et al. | |
| RE40,237 E | 4/2008 | Bilotti et al. | |
| 7,357,287 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,371,244 B2 | 5/2008 | Chatlynne et al. | |
| 7,380,695 B2 | 6/2008 | Doll et al. | |
| 7,380,696 B2 | 6/2008 | Shelton, IV et al. | |
| 7,390,329 B2 | 6/2008 | Westra et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,407,505 B2 | 8/2008 | Sauer et al. | |
| 7,410,086 B2 | 8/2008 | Ortiz et al. | |
| 7,416,101 B2 | 8/2008 | Shelton, IV et al. | |
| 7,416,554 B2 | 8/2008 | Lam et al. | |
| 576,278 A1 | 9/2008 | Nalagatla et al. | |
| 7,419,080 B2 | 9/2008 | Smith et al. | |
| 7,422,139 B2 | 9/2008 | Shelton, IV et al. | |
| 8,100,923 B2 * | 1/2012 | Paraschac et al. | 606/148 |
| 1,037,864 A1 | 9/2012 | Carlson | |
| 2002/0116010 A1 | 8/2002 | Chung et al. | |
| 2002/0116011 A1 | 8/2002 | Chee Chung et al. | |
| 2002/0198542 A1 | 12/2002 | Yamamoto et al. | |
| 2003/0045891 A1 | 3/2003 | Yamamoto et al. | |
| 2003/0181924 A1 | 9/2003 | Yamamoto et al. | |
| 2003/0216613 A1 | 11/2003 | Suzuki et al. | |
| 2004/0147941 A1 | 7/2004 | Takemoto et al. | |
| 2004/0186514 A1 | 9/2004 | Swain et al. | |
| 2005/0004584 A1 | 1/2005 | Franco et al. | |
| 2005/0113851 A1 | 5/2005 | Swain et al. | |
| 2005/0143762 A1 | 6/2005 | Paraschac et al. | |
| 2005/0149067 A1 | 7/2005 | Takemoto et al. | |
| 2005/0251165 A1 | 11/2005 | Vaughan et al. | |
| 2005/0277945 A1 | 12/2005 | Saadat et al. | |
| 2005/0277957 A1 | 12/2005 | Kuhns et al. | |
| 2005/0277981 A1 | 12/2005 | Maahs et al. | |
| 2006/0002852 A1 | 1/2006 | Saltzman et al. | |
| 2006/0004409 A1 | 1/2006 | Nobis et al. | |
| 2006/0004410 A1 | 1/2006 | Nobis et al. | |
| 2006/0015006 A1 | 1/2006 | Laurence et al. | |
| 2006/0015125 A1 | 1/2006 | Swain | |
| 2006/0020274 A1 | 1/2006 | Ewers et al. | |
| 2006/0025819 A1 | 2/2006 | Nobis et al. | |
| 2006/0036267 A1 | 2/2006 | Saadat et al. | |
| 2006/0155288 A1 | 7/2006 | Little et al. | |
| 2006/0167482 A1 | 7/2006 | Swain et al. | |
| 2006/0190016 A1 | 8/2006 | Onuki et al. | |
| 2006/0206063 A1 | 9/2006 | Kagan et al. | |
| 2006/0217762 A1 | 9/2006 | Maahs et al. | |
| 2006/0237022 A1 | 10/2006 | Chen et al. | |
| 2006/0237023 A1 | 10/2006 | Cox et al. | |
| 2006/0241691 A1 | 10/2006 | Wilk | |
| 2006/0253144 A1 | 11/2006 | Mikkaichi et al. | |
| 2006/0265010 A1 | 11/2006 | Paraschac et al. | |
| 2006/0271073 A1 | 11/2006 | Lam et al. | |
| 2006/0271101 A1 | 11/2006 | Saadat et al. | |
| 2006/0282089 A1 | 12/2006 | Stokes et al. | |
| 2006/0286664 A1 | 12/2006 | McAllister et al. | |
| 2007/0093858 A1 * | 4/2007 | Gambale et al. | 606/142 |
| 2007/0100375 A1 | 5/2007 | Mikkaichi et al. | |
| 2007/0100376 A1 | 5/2007 | Mikkaichi et al. | |
| 2007/0106313 A1 | 5/2007 | Golden et al. | |
| 2007/0112362 A1 | 5/2007 | Mikkaichi et al. | |
| 2007/0123840 A1 | 5/2007 | Cox | |
| 2007/0162052 A1 | 7/2007 | Hashimoto et al. | |
| 2007/0191886 A1 | 8/2007 | Dejima et al. | |
| 2007/0197864 A1 | 8/2007 | Dejima et al. | |
| 2007/0198000 A1 | 8/2007 | Miyamoto et al. | |
| 2007/0213702 A1 | 9/2007 | Kogasoka et al. | |
| 2007/0219411 A1 | 9/2007 | Dejima et al. | |
| 2007/0255296 A1 | 11/2007 | Sauer | |
| 2007/0270752 A1 | 11/2007 | LaBombard | |
| 2007/0270889 A1 | 11/2007 | Conlon et al. | |
| 2007/0276424 A1 | 11/2007 | Mikkaichi et al. | |
| 2008/0009888 A1 | 1/2008 | Ewers et al. | |
| 2008/0027272 A1 | 1/2008 | Kadykowski | |
| 2008/0048002 A1 | 2/2008 | Smith et al. | |
| 2008/0058710 A1 | 3/2008 | Wilk | |
| 2008/0058865 A1 | 3/2008 | Wilk | |
| 2008/0065157 A1 | 3/2008 | Crombie et al. | |
| 2008/0086153 A1 | 4/2008 | Sakamoto et al. | |
| 2008/0097489 A1 | 4/2008 | Goldfarb et al. | |
| 2008/0114378 A1 | 5/2008 | Matsushita | |
| 2008/0114379 A1 | 5/2008 | Takemoto et al. | |
| 2008/0114380 A1 | 5/2008 | Takemoto et al. | |
| 2008/0140095 A1 | 6/2008 | Smith et al. | |
| 2008/0147116 A1 | 6/2008 | Smith et al. | |
| 2008/0172088 A1 | 7/2008 | Smith et al. | |
| 2008/0177304 A1 | 7/2008 | Westra et al. | |
| 2008/0185752 A1 | 8/2008 | Cerwin et al. | |
| 2008/0200930 A1 | 8/2008 | Saadat et al. | |
| 2008/0208161 A1 | 8/2008 | Kaji et al. | |
| 2008/0208214 A1 | 8/2008 | Sato et al. | |
| 2008/0208218 A1 | 8/2008 | Shiono | |
| 2008/0208219 A1 | 8/2008 | Suzuki | |
| 2008/0208220 A1 | 8/2008 | Shiono et al. | |
| 2008/0208251 A1 | 8/2008 | Weadock et al. | |
| 2008/0221619 A1 | 9/2008 | Spivey et al. | |
| 2008/0228199 A1 | 9/2008 | Cropper et al. | |
| 2008/0228202 A1 | 9/2008 | Cropper et al. | |
| 2008/0228203 A1 | 9/2008 | Bell et al. | |
| 2008/0243148 A1 | 10/2008 | Mikkaichi et al. | |
| 2008/0255422 A1 | 10/2008 | Kondoh et al. | |
| 2008/0255423 A1 | 10/2008 | Kondo et al. | |
| 2008/0255427 A1 | 10/2008 | Satake et al. | |
| 2008/0262525 A1 | 10/2008 | Chang et al. | |

\* cited by examiner

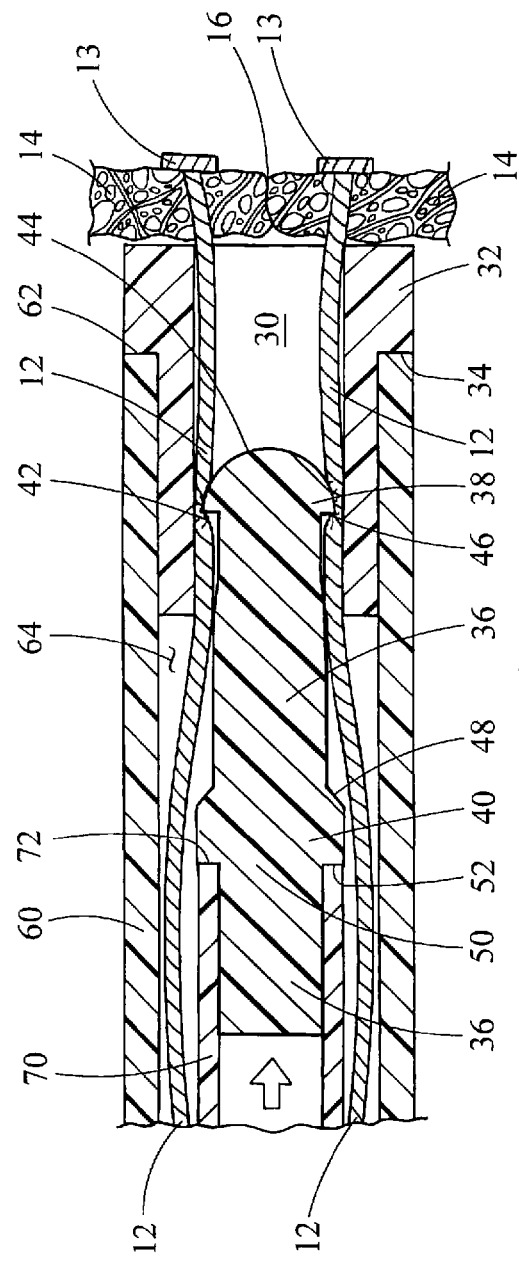
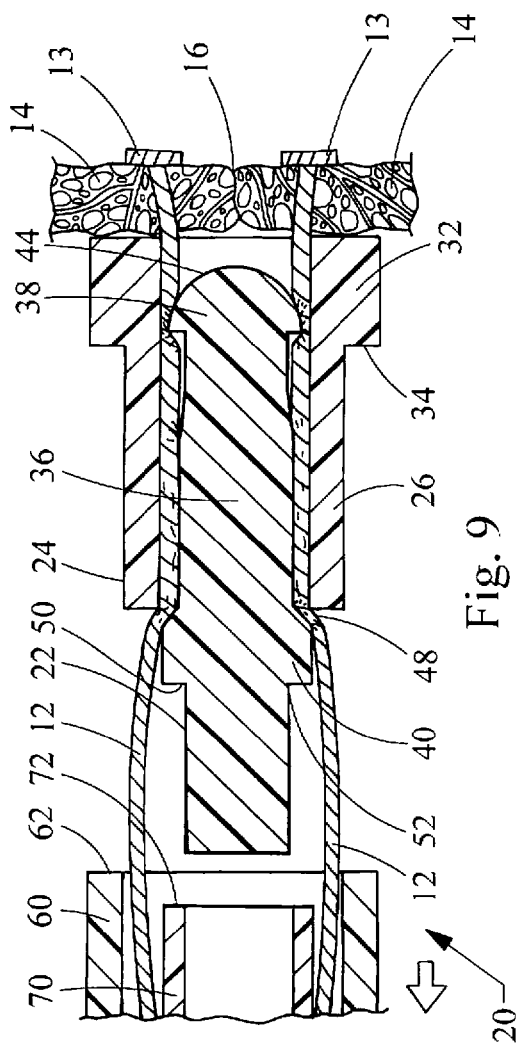

SUTURE LOCK

CROSS-REFERENCE TO RELATED APPLICATIONS

This application claims the benefit of U.S. Provisional Application Ser. No. 60/941,086 filed on May 31, 2007, entitled "SUTURE LOCK," the entire contents of which are incorporated herein by reference.

FIELD OF THE INVENTION

The present invention relates generally to suture locks for fixing the strands of one or more sutures relative to bodily tissue, such as for closing perforations in the tissue.

BACKGROUND OF THE INVENTION

Perforations in the walls of internal organs and vessels may be naturally occurring, or formed intentionally or unintentionally. In order to permanently close these perforations and allow the tissue to properly heal, numerous medical devices and methods have been developed employing sutures, adhesives, clips, staples, anchors and the like. Many of these devices typically employ one or more sutures, the strands of which must be brought together and fixed in place in order to close the perforation.

Manually tying sutures strands together to close a perforation can be very complex and time consuming. For example, a significant level of skill and coordination is required by the medical professional, especially when the perforation and sutures are difficult to access within the body, such as in endoscopic or laparoscopic procedures. The numerous difficulties with manually tying sutures are well documented. In order to address these and other issues of manual suture tying, various automatic suture tying systems have been developed. Unfortunately, such automatic systems are often complex and costly, difficult to use, and limited to use in certain situations.

BRIEF SUMMARY OF THE INVENTION

The present invention provides suture locks, as well as related systems and methods, for fixing strands of one or more sutures relative to tissue. The suture locks are simple and reliable in use, facilitate complete perforation closure and adjustment of the suture strands, and are adaptable to a variety of suture fixation and perforation closure situations. According to one embodiment of a suture lock constructed in accordance with the teachings of the present invention, the suture lock generally includes a locking pin and a retaining sleeve. The locking pin has a main body and a grip. The grip extends radially from the main body and defines an annular edge. The retaining sleeve has a tubular body within an internal wall defining an internal passageway sized to receive the locking pin therein. The suture lock is operable between a locked configuration and unlocked configuration. In the locked configuration, the suture strands are compressed between the grip and the internal wall of the tubular body.

According to more detailed aspects of the suture lock, the suture strands are compressed between the annular edge of the grip and the internal wall of the tubular body in the locked configuration. Preferably, the suture strands are also compressed between the main body and the internal wall of the tubular body in the locked configuration. The locking pin and retaining sleeve are connected in the locked configuration through their respective frictional engagement of the suture strands. In the locked configuration, the grip is structured to permit translation of the suture strands in a proximal direction (i.e. away from the tissue) and prevent translation of the suture strands in a distal direction (i.e. towards the tissue). The grip is preferably formed at a distal tip of the locking pin, and most preferably is dome-shaped.

Another embodiment of the present invention includes a system for fixing strands of one or more sutures relative to tissue. The system generally comprises a suture lock, a first pushing catheter, and a second pushing catheter. The suture lock includes a locking pin and a retaining sleeve. The retaining sleeve has a tubular body and includes a peripheral rim extending radially from the tubular body to define a first shoulder facing proximally. A stop extends radially from the main body to define a second shoulder facing proximally. The first pushing catheter defines a first lumen sized to receive the tubular body of the retaining sleeve and abut the first shoulder. The second pushing catheter defines a second lumen sized to receive the main body of the locking pin and abut the second shoulder.

According to more detailed aspects of the system, the first lumen of the first pushing catheter is sized to receive the second pushing catheter. Relative translation of the first pushing catheter and the second pushing catheter controls the relative positions of the retaining sleeve and the locking pin to operate the suture lock between a locked configuration and an unlocked configuration. The stop of the locking pin is sized to abut against the tubular body of the retaining sleeve to limit the relative positions of the locking pin and the retaining sleeve. The stop is also positioned relative to the grip to prevent the grip from passing completely through the internal passageway of the retaining sleeve. The suture strands pass through the second lumen of the second pushing catheter to a location outside of the body for manipulation thereof.

Another embodiment of the present invention provides a method for fixing strands of one or more sutures relative to tissue. The method generally comprises providing a suture lock, a first pushing catheter and a second pushing catheter, such as those described above. The retaining sleeve is engaged with the first pushing catheter, and the retaining sleeve is positioned proximate the tissue with the suture strands extending through the internal passageway of the retaining sleeve. The suture strands are placed in tension. The locking pin is engaged with the second pushing catheter and positioned within the internal passageway of the retaining sleeve such that the suture strands are compressed between the locking pin and the tubular body.

According to more detailed aspects of the method, the suture strands may be pulled in the proximal direction while pushing the second pushing catheter and the locking pin distally. The second pushing catheter and the locking pin are pushed distally relative to the first pushing catheter and retaining sleeve. The method may further include the steps of adjusting the tension on the suture strands. Preferably, the one or more sutures are placed around a perforation in the tissue, and the suture strands are placed in sufficient tension to close the perforation. The tension on the suture strands is maintained while the second pushing catheter and locking pin are pushed distally relative to the first pushing catheter and retaining sleeve. The frictional engagement of the locking pin with the suture strands, and of the retaining sleeve with the suture strands, is reinforced by the tension of the suture strands and the natural elasticity of the tissue.

BRIEF DESCRIPTION OF THE DRAWINGS

FIGS. 7-9 are cross-sectional views showing a system and method for deploying the suture lock depicted in FIG. 1.

DETAILED DESCRIPTION OF THE INVENTION

Figure 1:
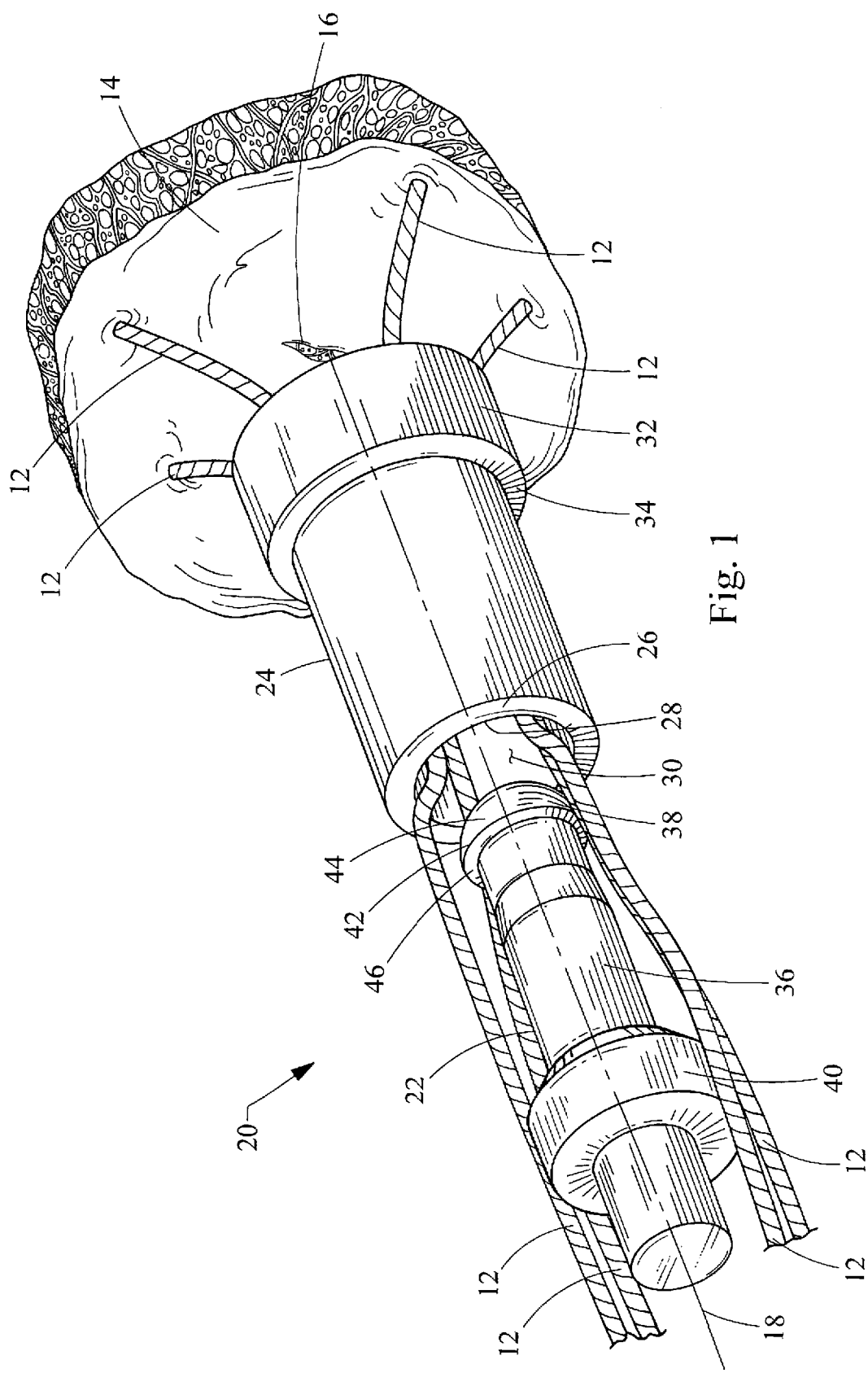
FIG. 1 is a perspective view of a suture lock constructed in accordance with the teachings of present invention.

Turning now to the figures, FIGS. 1-4 depict one embodiment of a suture lock 20 and its components, constructed in accordance with the teachings of the present invention. The suture lock 20 generally comprises a locking pin 22 and a retaining sleeve 24 which are used to fix the strands 12 of one or more sutures relative to bodily tissue 14, such as for closing a perforation 16 in the tissue 14. Preferably, the suture is formed of nylon 2-0 and of the monofilament variety, although any suture material or construction may be used with the suture lock 20 of the present invention. Generally, the suture strands 12 will be placed through the tissue 14 and connected thereto using standard suturing techniques or devices such as T-anchors, staples or the like, leaving the strands 12 on one side of the tissue 14 for tying them together. Although the retaining sleeve 24 and locking pin 22 have been depicted as having circular cross-sections, it will be recognized that other cross-sectional shapes may be used including triangular, square, etc.

Figure 4:
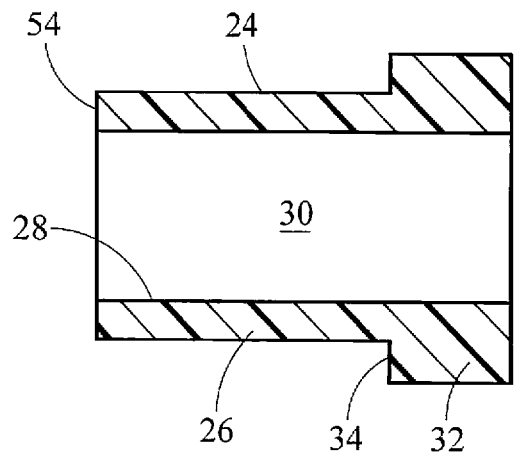
FIG. 4 is a cross-sectional view of a retaining sleeve forming a portion of the suture lock depicted in FIG. 1.

As best seen in FIG. 4, the retaining sleeve 24 generally comprises a tubular body 26 having an interior surface 28 defining an interior passageway 30. A peripheral rim 32 is formed at a distal end of the tubular body 26, and defines a shoulder 34 which is used for placement of the retaining sleeve 24, as will be discussed in further detail herein. Generally, the retaining sleeve 24 receives the suture strands 12 within the interior passageway 30. The suture strands 12 are then fixed in place using the locking pin 22, which is designed to fit within the passageway 30 and pinch or compress the suture strands 12. It will also be recognized that the locking pin 22 may have many configurations (e.g. solid, hollow, regular or irregular shapes), and constructions (e.g. cast, molded, machined, wound (such as with wire), etc.) so long as a portion of the locking pin 22 cooperates with the retaining sleeve 24 to fix the suture strands 12.

Figure 2:
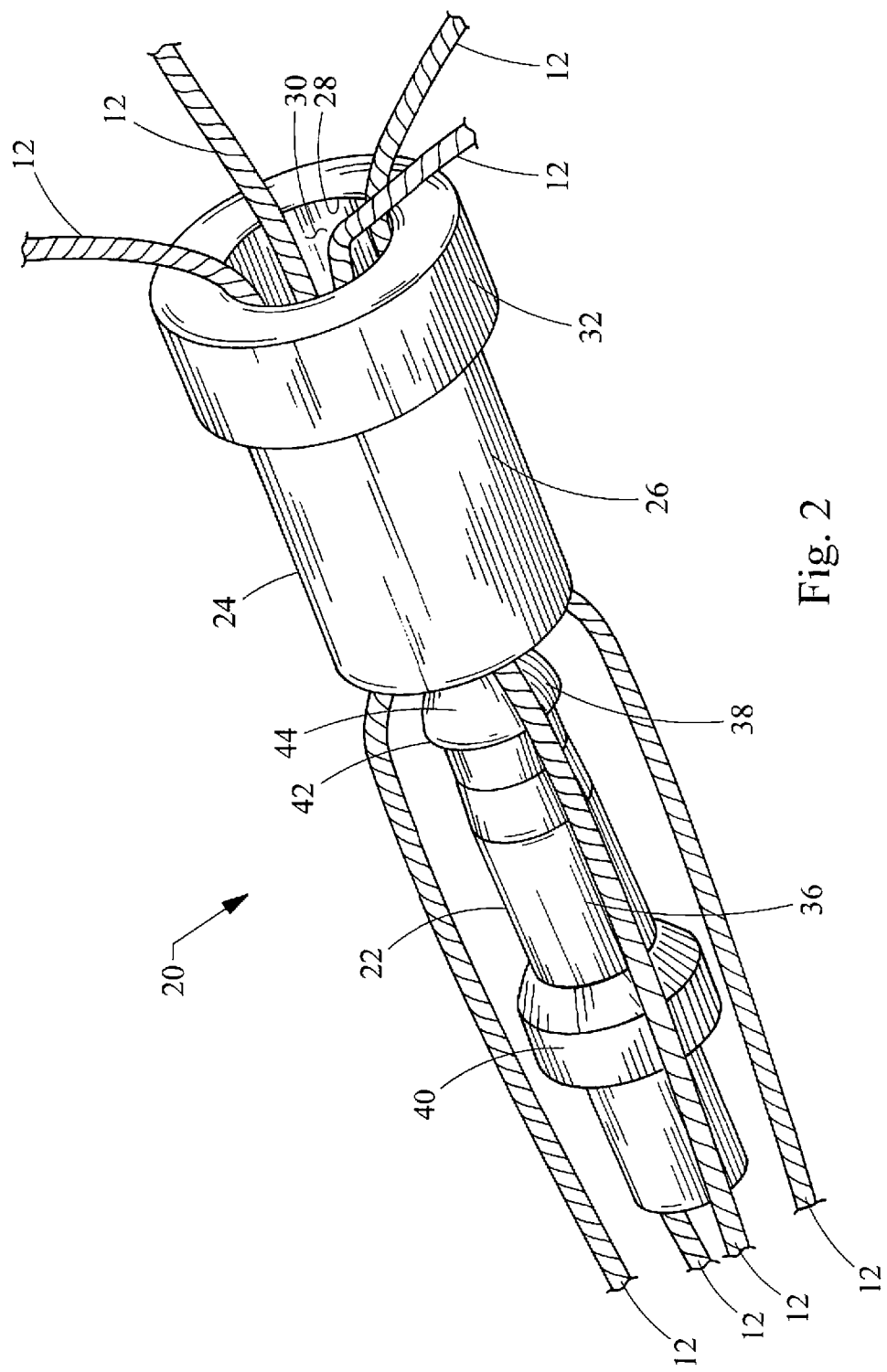
FIG. 2 is another perspective view of the suture lock depicted in FIG. 1.
Figure 3:
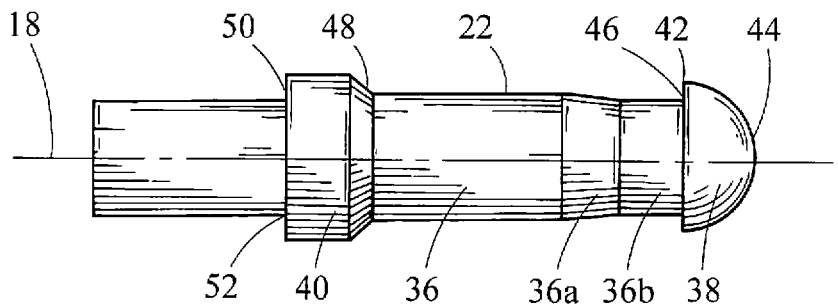
FIG. 3 is a side view of a locking pin forming a portion of the suture lock depicted in FIG. 1.

As best seen in FIG. 3, the locking pin 22 generally comprises a main body 36, a grip 38, and a stop 40. The main body 36 defines a longitudinal axis 18, and both the grip 38 and stop 40 extend radially from the main body 36. In the illustrated embodiment, the grip 38 is formed at a distal end of the locking pin 22, although it could be moved proximally along the length of the main body 36. The grip 38 defines an annular edge 42 that is used to engage the suture strands 12, as will be discussed in more detail herein. The grip 38 includes a leading surface 44 located distally of the annular edge 42, and a trailing surface 46 located proximally of the annular edge 42. The leading surface 44 tapers, and most preferably is curved such as the dome-shaped surface (e.g., semi-spherical) shown in FIGS. 1-3. At the same time, the trailing surface 46 is generally transverse to the longitudinal axis 18. While the trailing surface 46 has been shown as perpendicular to the longitudinal axis 18 in the figures, any shape or angle relative to the leading surface 44 which is sufficient to define the annular edge 42 suitable for gripping the suture strands 12 is encompassed herein and by the use of the term "transverse." As shown in FIG. 3, the main body 36 also includes a tapered portion 36a and reduced diameter portion 36b located between the grip 38 and stop 40.

The stop 40 is longitudinally spaced from the grip 38 and is used to control the position of the locking pin 22 within the retaining sleeve 24. The stop 40 generally includes a distally facing surface 48 and a proximally facing surface 50. The proximally facing surface 50 and main body 36 define a shoulder 52 which is used to position the locking pin 22, as will be discussed in more detail herein. The stop 40 is positioned relative to the grip 38 to prevent the grip 38 from passing completely through the internal passageway 30 of the retaining sleeve 24.

Figure 5:
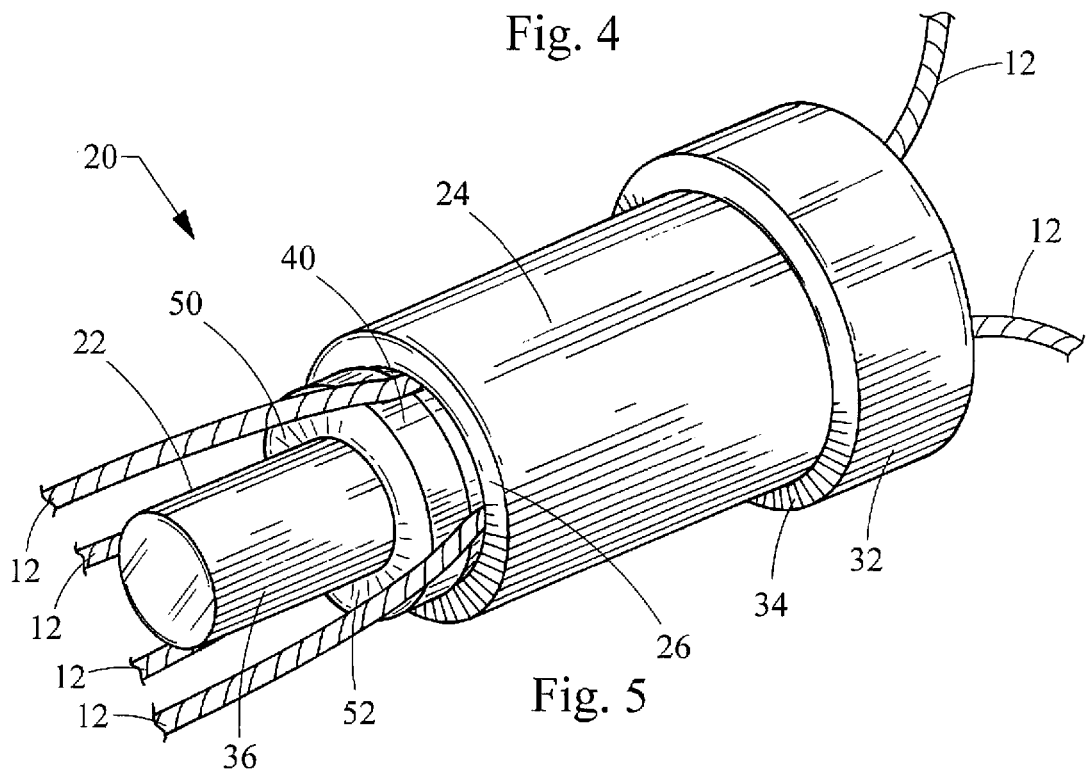
FIG. 5 is a perspective view of the suture lock depicted in FIG. 1, showing the suture lock in a locked configuration.
Figure 6:
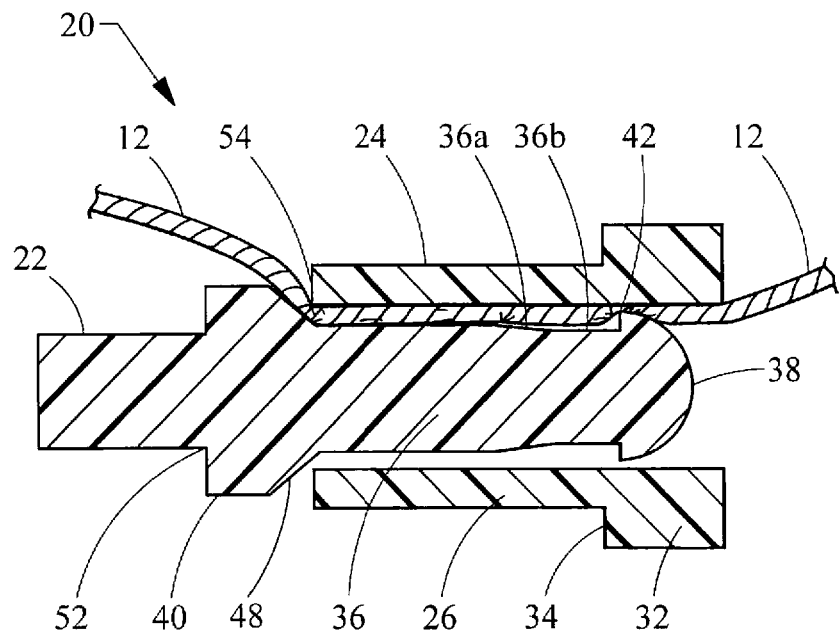
FIG. 6 is cross-sectional view of the suture lock as depicted in FIG. 5.

Interconnection of the locking pin 22 and retaining sleeve 24 will now be described with reference to FIGS. 5 and 6, which depict a locked configuration of the suture lock 20 (the unlocked configuration being shown in FIGS. 1 and 2). Generally, the interior passageway 30 of the retaining sleeve 24 is sized to receive at least a portion of the locking pin 22 therein. In the locked configuration, the main body 36 and grip 38 are received within the interior passageway 30 of the retaining sleeve 24. As best seen in FIG. 6, the suture strands 12 are compressed between the grip 38 and the interior surface 28 of the tubular body 26. As the locking pin 22 is advanced (i.e. distally) from left to right in FIG. 6, the tapered leading surface 44 of the grip 38 allows the locking pin 22 to be translated distally relative to the suture strands 12 and retaining sleeve 24. However, due to the generally sharp annular edge 42, it is more difficult to move the suture strands 12 distally relative to the locking pin 22. In this manner, the suture strands 12 are maintained in a fixed relationship relative to one another and to the tissue 14.

As will be described in more detail herein, the suture strands 12 are generally in tension, due in part to the natural elasticity of the bodily tissue 14, which generally attempts to pull the suture strands 12 distally. Accordingly, while the locking pin 22 may be advanced through the retaining sleeve 24 and slid along the suture strands 12, the tension on the suture strands 12 also exerts a distally directed force on the locking pin 22 via the grip 38 and its annular edge 42. As such, the suture lock 20 is a form of self-motivating locking device that promotes secure fixation of the suture strands 12 relative to the tissue 14. At the same time, the suture strands 12 may be pulled in the proximal direction to adjust suture tension, suture lock position, and/or perforation closure, even when the suture lock 20 is in the locked configuration.

It can also be seen in FIG. 6 that the main body 36 is sized to at least partially compress the suture strand 12 against the interior surface 28 of the tubular body 26. At the same time, the tapered portion 36a and reduced diameter portion 36b provide an area of limited or no contact with the suture strand 12. These areas may be sized to adjust the level of friction between the suture strands 12 and the suture lock 20, for example based on the type and size of suture material. The stop 40 abuts against a proximal end surface 54 of the tubular body 26, thereby limiting the position of the locking pin 22 within the retaining sleeve 24. The distally facing surface 48 of the stop 40 is generally tapered to slightly compress the suture strands 12 against the tubular member 26, while still allowing the suture strands 12 to exit the suture lock 20 and be translated in a proximal direction.

The components of the suture lock may be constructed of various materials, such as stainless steel, titanium, nitinol or other metals/alloys, although various ceramics or plastics can also be employed, such as polycarbonates (PC), polyamides including Nylon(TM), polytetrafluorethylenes (i.e. PTFE and EPTFE), polyethylene ether ketones (PEEK), polyvinylchlorides (PVC), polyimides, polyurethanes, and polyethylenes (high, medium or low density), including multi-layer or single layer constructions with or without reinforcement wires, coils or filaments.

Figure 7:
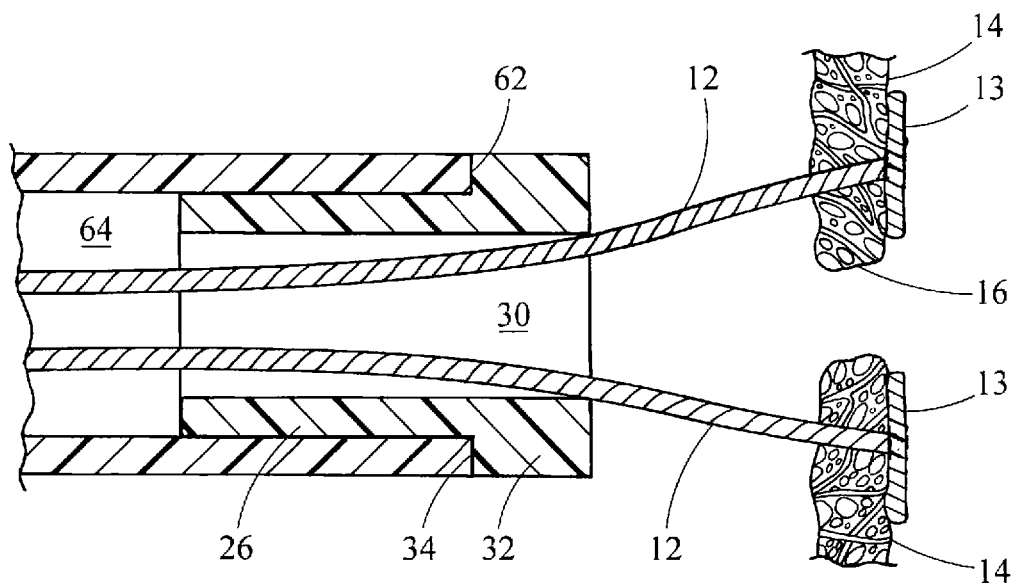

A system and method for employing the suture lock 20 will now be described with reference to FIGS. 7-9. As shown in FIG. 7, the suture strands 12 have been placed through the tissue 14 in proximity to the perforation 16, such as by using T-anchors 13. T-anchors are well known in the art, exemplary T-anchors being disclosed in U.S. Pat. No. 5,123,914 and U.S. patent application Ser. No. 11/946,565 the disclosures of which are incorporated herein by reference in their entireties. The retaining sleeve 24 is fitted onto a distal end of a first pushing catheter 60. The pushing catheter 60 may take the form of any catheter or cannula known in the art, but preferably has sufficient strength and rigidity for both longitudinal and rotational force transmission, while still providing flexibility for navigation of a patient's body. Exemplary pushing catheters are sold by Cook Incorporated and Wilson-Cook Medical, Inc. It will also be recognized that other pushers or pushing elements may be employed, such as solid wires or wire guides, clamps, graspers and the like. Magnets could likewise be employed to releasably connect the pusher to the retaining sleeve 24.

The pushing catheter 60 has a distal end surface 62 and a first lumen 64. The first lumen 64 is sized to receive the tubular body 26 of the retaining sleeve 24, while the distal end surface 62 of the pushing catheter 60 abuts against the shoulder 34 of the retaining sleeve 24. Generally, the pushing catheter 60 and retaining sleeve 24 are loosely press fit such that the retaining sleeve 24 may be readily controlled and positioned using the catheter 60. Likewise, the retaining sleeve 24 maintains its connection to the catheter during placement of the locking pin 22 within the sleeve 24, while at the same time the retaining sleeve 24 is also readily disconnected from the pushing catheter 60 at the end of the procedure. It will be recognized that the pushing catheter 60 and retaining sleeve 24 need not be sized to frictionally engage, as the tensioned suture strands 12 and the tissue 14 will generally maintain the position of the retaining sleeve 24 on the pushing catheter 60 during placement of the locking pin 22, such as is shown in FIGS. 8 and 9.

With reference to FIG. 7, the suture strands 12 are threaded through the interior passageway 30 of the retaining sleeve 24 and through the first lumen 64 of the first pushing catheter 60. The pushing catheter 60 is used to distally translate the retaining sleeve 24 over the suture strands 12 to a position proximate the tissue 14 and perforation 16. The suture strands 12 are tensioned in order to draw the perforation 16 closed and press the tissue against the peripheral rim 32 of the retaining sleeve 24.

As shown in FIG. 8, a second pushing catheter 70 is loosely press fit with the locking pin 22, although the two structures may simply abut each other for longitudinal translation. The second pushing catheter 70 may have a construction similar to the first pushing catheter 60 or other pusher described above. In the depicted embodiment, the second pushing catheter 70 includes a distal end 72 and second lumen 74 which are sized to abut against the shoulder 52 and receive the main body 36 of the locking pin 22, respectively. Accordingly, the second pushing catheter 70 is connected to the locking pin 22 and together they are translated distally through the first lumen 64 of the first pushing catheter 60. The locking pin 22 is pressed into engagement with the retaining sleeve 24 to fix the suture strands 12 therebetween. With the suture strands 12 in tension (e.g. by pulling them in a proximal direction), the locking pin 22 is advanced through the interior passageway 30 of the retaining sleeve 24, whereby the suture strands 12 are compressed between the grip 38 and the interior surface 28 of the retaining sleeve 24. It can therefore be seen that relative translation of the first pushing catheter 60 and the second pushing catheter 70 controls the relative positions of the retaining sleeve 24 and locking pin 22 to operate the suture lock 20 between a locked configuration and an unlocked configuration.

As previously discussed, the leading surface 44 of the grip 38 is slid along the suture strands 12 as the locking pin 22 is distally advanced through the interior passageway 30. With further advancement, the main body 36 also engages the suture strands 12 and at least partially compresses them against the interior surface 28 of the retaining sleeve 24. The annular shape of the grip 38 allows the suture strands 12 to be positioned anywhere around the outer periphery of the grip 38 and locking pin 22. Distal movement of the locking pin 22 is eventually limited by the stop 40, and namely the distally facing surface 48 of the stop 40 abutting against the proximal end surface 54 of the retaining sleeve 24. The tension on the suture strands 12 grips into the annular edge 42 of the grip 38, and serves to promote movement of the locking pin 22 in the distal direction, as well as resist proximal movement and unlocking of the suture lock 20.

When in the locked configuration (and when partially locked such as when the locking pin 22 partially placed within the retaining sleeve 24 but not fully seated), the grip 38 is structured to permit further translation of the suture strands 12 proximally, i.e. away from the tissue 14, and prevent translation of the suture strands 12 distally, i.e. towards the tissue 14. Further, the suture strands 12 may be individually pulled or tensioned in order to orient the suture lock 20 relative to the bodily tissue 14 and perforation 16, even when the suture strands 12 are compressed by the locking pin 22 and retaining sleeve 24, such as when the suture lock 20 is in the locked configuration. As such, tension on the suture strands 12 may be modified to adjust how the perforation 16 is closed. This represents a marked improvement over existing suture locks, which typically are permanently fixed in position along the sutures such that adjustment during and after the locking procedure, i.e. in partially locked and finally locked configurations, is not possible.

In the fully locked condition, as shown in FIG. 9, the tension on the suture strands 12, as well as the natural elasticity of the tissue 14, result in a force being transmitted through the suture strand 12 to the grip 38 biasing it in the distal direction. In this manner, the retaining sleeve 24 and locking pin 22 are interconnected through their respective frictional engagement with the suture strands 12 and compression thereof. In the locked condition, the first and second pushing catheters 60, 70 are easily removed from the retaining sleeve 24 and locking pin 22, respectively, and may be withdrawn from the patient. The suture strands 12 may be trimmed as necessary. To release the suture lock, the suture strands 12 may be cut, or the first pushing catheter 60 may be used to hold the retaining sleeve 24 while the retaining pin 22 is grasped (such as with a snare, forceps, or similar device) and physically withdrawn against the friction and tension of the suture strands 12.

Accordingly, the present invention provides a suture lock, as well as a system and method for deploying the suture lock, which is simple and reliable in use, provides complete perforation closure, and which is adaptable to a variety of suture fixation and perforation closure applications. For example, any number of suture strands may be employed and the relative sizes of the locking pin and retaining sleeve may be adjusted based on suture size, perforation size and the like. The interconnection of the locking pin and retaining sleeve is such that the suture lock is self-motivated and biased towards a locked configuration, thereby assisting and promoting complete perforation closure as well as control over the position of the suture lock relative to the tissue being sutured through adjustment of the suture strands even when they are compressed. Adjustment of individual suture tension and location of the suture lock are also possible during and after placement of the suture lock. At the same time, the two pushing catheters provide a simple system for deployment of the suture anchor that can be traversed through the body of a patient to even the most remote locations.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A suture lock for fixing strands of one or more sutures relative to tissue, the suture lock comprising:
   a suture strand;
   a locking pin having a main body and a grip formed at a distal tip of the main body, the main body defining a longitudinal axis, the grip extending radially from the main body and defining an annular edge, the grip including a leading surface located distally of the annular edge and a trailing surface located proximally of the annular edge, the leading surface being tapered from the annular edge towards the longitudinal axis;
   a retaining sleeve having a tubular body with an internal wall defining an internal passageway sized to receive the locking pin and its grip therein, the internal passageway having a uniform diameter along the longitudinal length of the tubular body; and
   the suture lock being operable between a locked configuration and an unlocked configuration, the locking pin and the retaining sleeve being connected in the locked configuration and being separated in the unlocked configuration, the locking pin and the retaining sleeve sized and structured to compress the suture strand between the grip and the internal wall of the tubular body, and between the main body and the internal wall of the tubular body, in the locked configuration, the main body defining a reduced diameter portion proximal to the grip, the reduced diameter portion sized relative to the internal wall to not compress the suture strand between the reduced diameter portion and the internal wall.

2. The suture lock of claim 1, wherein the suture strands are compressed between the annular edge of the grip and the internal wall of the tubular body in the locked configuration.

3. The suture lock of claim 1, wherein, in the locked configuration, the leading and trailing surfaces of the grip are structured to permit translation of the suture strands in a proximal direction and prevent translation of the suture strands in a distal direction.

4. The suture lock of claim 1, wherein the leading surface of the grip is dome-shaped.

5. The suture lock of claim 1, wherein the leading surface is curved.

6. The suture lock of claim 1, wherein the trailing surface is transverse to the longitudinal axis.

7. The suture lock of claim 1, wherein the reduced diameter portion is immediately proximal to the grip.

8. The suture lock of claim 1, wherein the main body defines a tapered portion proximal to the grip, the tapered portion having diameters smaller than an adjacent portion of the main body to reduce the friction between the suture strands, the locking pin and the sleeve proximate the tapered portion.

9. The suture lock of claim 1, further comprising a stop extending radially from the main body and positioned to abut the retaining sleeve.

10. The suture lock of claim 9, wherein the stop extends entirely around the periphery of the main body of the locking pin.

11. The suture lock of claim 1, wherein the stop includes a distally facing surface and a proximally facing surface, the distally facing surface being tapered towards the main body.

12. The suture lock of claim 1, wherein the reduced diameter portion has a uniform diameter along its length.

13. A suture lock for fixing strands of one or more sutures relative to tissue, the suture lock comprising:
   a locking pin having a main body and a grip, the main body defining a longitudinal axis, the grip extending radially from the main body and defining an annular edge, the grip including a leading surface located distally of the annular edge and a trailing surface located proximally of the annular edge, the leading surface being tapered from the annular edge towards the longitudinal axis;
   a retaining sleeve having a tubular body with an internal wall defining an internal passageway sized to receive the locking pin and its grip therein; and
   the suture lock being operable between a locked configuration and an unlocked configuration, the locking pin and the retaining sleeve being connected in the locked configuration and being separated in the unlocked configuration, the locking pin and the retaining sleeve sized and structured to compress a suture strand between the grip and the internal wall of the tubular body in the locked configuration;
   wherein the locking pin has stop extending radially from the main body at a location distal to a proximal end of the locking pin to define a second shoulder facing proximally, the stop having a distally facing surface sized and positioned to abut a proximal end surface of the tubular body of the retaining sleeve, the distally facing surface tapered towards the longitudinal axis and wherein the retaining sleeve includes a peripheral rim extending radially from the tubular body to define a first shoulder facing proximally, and further comprising a first pushing catheter defining a first lumen sized to receive the tubular body of the retaining sleeve and abut the first shoulder, and a second pushing catheter defining a second lumen sized to receive the main body of the locking pin and abut the second shoulder.

14. The suture lock of claim 13, wherein the first lumen of the first pushing catheter is sized to receive the second pushing catheter.

15. The suture lock of claim 13, wherein the stop of the locking pin is sized to abut against the tubular body of the retaining sleeve to limit the position of the locking pin relative to the retaining sleeve.

16. The suture lock of claim 13, wherein the stop extends entirely around the periphery of the main body of the locking pin.

17. The suture lock of claim 13, wherein, in the locked configuration, the leading and trailing surfaces of the grip, and the distally facing surface of the stop, are structured to permit translation of the suture strands in a proximal direction and prevent translation of the suture strands in a distal direction.

18. The suture lock of claim 13, wherein the second lumen of the second pushing catheter is sized to provide a friction fit with the proximal end of the locking pin.

19. The suture lock of claim 13, wherein, the second lumen of the second pushing catheter is sized to provide a friction fit with the proximal end of the locking pin, and that the first lumen of the first pushing catheter is sized to provide a friction fit with the retaining sleeve.

\* \* \* \* \*